United States Patent
Attali et al.

(10) Patent No.: US 8,592,434 B2
(45) Date of Patent: *Nov. 26, 2013

(54) MUCOADHESIVE BUCCAL TABLETS FOR THE TREATMENT OF OROFACIAL HERPES

(75) Inventors: Pierre Attali, Vincennes (FR);
Dominique Costantini, Paris (FR);
Caroline Lemarchand, Paris (FR)

(73) Assignee: BioAlliance Pharma SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 12/634,225

(22) Filed: Dec. 9, 2009

(65) Prior Publication Data

US 2011/0136837 A1    Jun. 9, 2011

(51) Int. Cl.
*A01N 43/90* (2006.01)
*A01N 43/42* (2006.01)
*A61K 31/522* (2006.01)
*A61K 31/44* (2006.01)

(52) U.S. Cl.
USPC ............... 514/263.38; 514/283; 514/934

(58) Field of Classification Search
USPC .................. 514/263.38, 283, 934
See application file for complete search history.

(56) References Cited

U.S. PATENT DOCUMENTS

| | | |
|---|---|---|
| 6,916,485 B2 | 7/2005 | Aiache et al. |
| 7,651,698 B2 | 1/2010 | Aiache et al. |
| 2003/0108603 A1 | 6/2003 | Aiache et al. |
| 2009/0169511 A1 | 7/2009 | Costantini et al. |

FOREIGN PATENT DOCUMENTS

| | | |
|---|---|---|
| WO | WO 95/15137 A1 | 6/1995 |
| WO | WO 01/82905 A1 | 11/2001 |
| WO | WO 2007/110778 A2 | 10/2007 |
| WO | WO 2009/049648 A2 | 4/2009 |

OTHER PUBLICATIONS

Whitley (Seminars in Pediatric Infectious Diseases, 13, 1, 2002, 6-11).*
Opstelten et al., "Treatment and prevention of herpes labialis," Canadian Family Physician, vol. 54, Dec. 2008, pp. 1683-1687.
Parry et al., "Acyclovir bioavailability in human skin," Journal of Investigative Dermatology, vol. 98, No. 6, Jun. 1992, pp. 856-863.
Raborn et al., "Herpes labialis in skiers," Oral Surgery, Oral Medicine, Oral Pathology, Oral Radiology and Endodontics, vol. 84, No. 6, Dec. 1997, pp. 641-645.
Raborn et al., "Oral acyclovir and herpes labialis: a randomized, double-blind, placebo-controlled study," Journal of the American Dental Association, vol. 115, Jul. 1987, pp. 38-42.
Rooney et al., "Oral acyclovir to suppress frequently recurrent herpes labialis, a double-blind, placebo-controlled trial," Annals of Internal Medicine, vol. 118, No. 4, Feb. 15, 1993, pp. 268-272.
Spruance et al., "Acyclovir cream for treatment of herpes simplex labialis: results of two randomized, double-blind, vehicle-controlled, multicenter clinical trials," Antimicrobial Agents and Chemotherapy, vol. 46, No. 7, Jul. 2002, pp. 2238-2243.
Spruance et al., "Clinical significance of antiviral therapy for episodic treatment of herpes labialis: exploratory analyses of the combined data from two valaciclovir trials," Journal of Antimicrobial Chemotherapy, vol. 53, No. 5, 2004, pp. 703-707.
Spruance et al., "High-dose, short-duration, early valacyclovir therapy for episodic treatment of cold sores: results of two randomized, placebo-controlled, multicenter studies," Antimicrobial Agents and Chemotherapy, vol. 47, No. 3, Mar. 2003, pp. 1072-1080.
Spruance et al., "Treatment of herpes simplex labialis," Herpes, vol. 9, No. 3, 2002, pp. 64-69.
Spruance et al., "Treatment of recurrent herpes simplex labialis with oral acyclovir," The Journal of Infectious Diseases, vol. 161, 1990, pp. 185-190.
Zakay-Rones et al., "Hypothesis: the gingival tissue as a reservoir for herpes simplex virus," Microbiologica, vol. 9, 1986, pp. 367-371.
International Search Report from PCT/EP2010/069313 dated Feb. 9, 2011.
De Vries M. E. et al., 1991, "Developments in buccal drug delivery," *Critical Reviews in Therapeutic Drug Carrier Systems* 8(3):271-303, 290, 293-298.
Thomas et al., 1985, "Oral acyclovir in the suppression of recurrent non-genital herpes simplex virus infection", *British Journal of Dermatology* (113):731-735.
BioAlliance Pharma S.A., "BioAlliance Pharma announces positive preliminary pivotal phase III results in herpes labialis with acyclovir Lauriad®," Aug. 26, 2009.

* cited by examiner

*Primary Examiner* — Sreeni Padmanabhan
*Assistant Examiner* — Uma Ramachandran
(74) *Attorney, Agent, or Firm* — Dechert LLP

(57) ABSTRACT

The present invention relates to the treatment or prevention of mucocutaneous herpes simplex virus diseases using prolonged release mucoadhesive buccal tablets comprising an acyclic guanosine antiviral agent. These tablets are particularly suitable for the treatment or prevention of orofacial herpes.

22 Claims, 4 Drawing Sheets

MUCOADHESIVE BUCCAL TABLETS FOR THE TREATMENT OF OROFACIAL HERPES

TECHNICAL FIELD

The present invention relates to the treatment or prevention of mucocutaneous herpes simplex virus diseases using prolonged release mucoadhesive buccal tablets comprising an acyclic guanosine antiviral agent. These tablets are particularly suitable for the treatment or prevention of orofacial herpes.

BACKGROUND OF THE INVENTION

Herpes Simplex Virus (HSV) is the most widely spread virus in the herpes family. It has been identified as the pathogenic agent in a number of infectious processes involving the mucocutaneous tissues, the nervous central system, and in severe cases, the viscera. About one billion people worldwide have been infected with herpes viruses that belong to two types according to the antigenic differences in the envelope proteins: HSV type 1 (HSV-1) and HSV type 2 (HSV-2). The largest reservoir of HSV is associated with herpes labialis, most commonly resulting from primary infection with HSV-1 during childhood. The prevalence of HSV-1 and HSV-2 is estimated to be between 50-95% and 6-50% respectively, depending on several factors such as age, race, sex, marital and social status. HSV-1 primarily causes oral infections, whereas HSV-2 is the most common cause for genital ulcers.

Herpes labialis (also known as "orofacial herpes", "orolabial herpes", "cold sores" or "fever blisters") is the most common recurrent infection caused by HSV-1 with considerable incidence (85% of the world's population is seropositive for HSV-1). In many cases, it causes blisters or sores on or around the mouth that are commonly known as cold sores or fever blisters. Hence, it is aesthetically unpleasant and induces considerable discomfort to the patient. Sores associated with herpes labialis typically heal within 2-3 weeks, but the virus that causes them is not removed from the body. Recurrent episodes of herpes labialis are frequent. That means that the infected herpes virus becomes dormant in the facial nerves, following orofacial infection, periodically reactivating to create sores in the same area of the mouth or face that the original infection occurred.

It is estimated that about 20-40% of people have experienced orofacial herpes at some time. In Europe, the overall incidence is approximately 3 per 1000 people per year and more than 10 per 1000 people per year in those aged over 80 years. In the United States, approximately 130 million individuals over 12 years are infected with HSV-1. Approximately one third of the patients with HSV-1 infection will experience recurrent episodes of herpes labialis.

Most people acquire HSV-1 asymptomatically. Primary infection usually occurs in childhood. It is usually asymptomatic, but may present in different forms: transient gingivostomatitis, pharyngitis or other lesions in and the oral cavity, sometimes with fever.

HSV infects mucous membranes, replicates at the cutaneous entry site (cells of the epidermis and dermis) and may infect the sensory nerve ending that innervate cells at the initial infection site provided that the number of virions is sufficient. The virus is then transported to the sensory nerve nuclei, the trigeminal ganglion for herpes labialis, and remains in a latent state in sensory neurons for the life of the host cell. HSV reactivation could occur in a fraction of population harbouring the latent virus. Upon reactivation, HSV could disseminate throughout the axon from infected cells to the mucosa. Hence, as HSV remains in the mammalian body, orofacial herpes is a recurrent disease. That means that, following reactivation of latent HSV, patients undergo many occurrences of herpes labialis throughout their life. A main challenge for current herpes labialis treatment is to lower the frequency, duration, and severity of these occurrences. The reservoir site of persistent HSV, from the primary infection until reactivation and in between recurrences was found to be in the dorsal roots of the trigeminal ganglion or in the sensory root ganglion. However, the triggering of the viral genome in the ganglion does not exclusively explain the recurrences of herpes labialis. Other sites can be infected with HSV. It was suggested in the state of the art that HSV may well be occult in epithelial cells. Hence, mucous and skin cells might also act as a preferential site for latent HSV (Zakay-Rones Z., Microbiologica, 1986).

Moreover, the viral load in saliva during herpes labialis occurrences increases the persistence of HSV. Indeed, high concentrations of virions in saliva lead to reinfestations through the mucous membranes of the mouth. Such infections further supply the HSV reservoir and thus the latency of HSV.

Up to now no herpes labialis treatment acts on the reservoir of latent HSV.

Reactivation may be triggered by several factors that are specific to the patient, i.e., emotional stress, fever, exposure to ultraviolet light, menses, premenstrual tension, surgical (such as dental or neural) procedures, lip tattooing, dermabrasion or oral traumas. Immune suppression also favours reactivation.

The clinical manifestations of herpes labialis infection depend largely on the anatomic site of infection, immune status of the host and the antigenic type of virus. Most lesions occur on the lips. However, lesions can also occur on the nose, cheeks, or chin. Lesions occurring in the oral cavity or face are less common. Intra-oral lesions are hard to locate and are difficult to distinguish from apthous ulcers, oropharyngeal candidiasis or cancer sores.

In the immunocompetent population, occurrence of herpes labialis follows a predictable course (schematized in FIG. 1), called episodes. An episode of herpes labialis comprises:

Prodrome: episodes of herpes labialis begin with a prodromal stage, during which patients experience pain, burning, itching, tingling, or discomfort in the area of the lesion. It is thus the patient's first indication that herpes labialis is developing. The prodromal stage reliably predicts the onset of lesion outbreak.

Erythema: erythema, a redness of the skin may be present but does not always appear in every patient.

Papula: progression to lesion outbreak is rapid. Clinical manifestations of the lesion are papules (small, solid, inflammatory elevations of the skin that does not contain pus) or indurations of the skin.

Vesicle: within the next 12 hours, lesions of maximal severity, known as cold sores or fever blisters appear on the vermillion border of the lip as multiple, fluid filled vesicles that tend to rupture rapidly and to become confluent into an ulcer in 72-96 hours. The lesion area and pain are generally maximum within 24 hours. This is also the stage at which a cold sore is most contagious.

The first cold sores or fever blisters are named primary vesicles (or primary vesicular lesions). Sometimes, patients present secondary vesicles (or secondary vesicular lesions) which are other cold sores or fever blisters appearing after and around the first vesicles.

Crust: then, the ulcer progresses to a crusting stage. In those areas where the cold sore lesion is not kept wet by moisture from the mouth the ulcer will become dry and scab over with a brownish crust. The formation of this scabbing is often accompanied by an itching or burning sensation. Often the scab will crack or break, which in turn produces bleeding. As time progresses so will the cold sore's healing.

Erythema: during the healing erythema, a redness of the skin may be present but does not always appear in every patient.

Healing/normal skin: the cold sore resolves itself fully, usually without scarring.

Herpes labialis typically resolves spontaneously within about 7-14 days. Although most of the episodes are mild, some may be severe or disfiguring, causing psychological distress and physical discomfort.

On average, 25% of all episodes do not progress beyond the papule stage. These are called "aborted" (or "abortive" or "non vesicular") episodes. About one-half of these do not progress beyond the prodromal stage.

Patients may undergo recurrent episodes throughout their life. That means that they have to manage several herpes labialis occurrences throughout their life. The infection is transmitted when the virus is present. The amount of virus is highest within the first eight hours of lesion development and diminishes as the lesions mature. Herpes labialis is spread through saliva or through the direct contact of skin or mucus membranes with lesions or oral secretions of an infected person. Risk of transmission often increases in day care settings due to the large numbers of children who are in close proximity to each other. Most of the transmission in these settings is believed to be asymptomatic. Transmission in households is believed to be from kissing, though it is good to avoid sharing cups, eating utensils, wash cloths, etc. when one has a visible sore.

In HIV patients, herpes labialis appears as chronic, hyperproliferative plaques different from the classic acute mucocutaneous ulcerative lesions and may be related to resistant isolates.

Historically, the difficulty in treating herpes labialis has been attributed to the rapid development of lesions, natural history of viral infection and a strong secondary immunological response that limits lesion duration in untreated patients.

Viral replication is most active before prodromal symptoms or in the first 8 hours after their occurrence and a window of opportunity for antiviral agents may exist when adequate concentrations are used and treatment is initiated during the time that viral replication dominates temporarily the host immune response. Consequently, early high dose antiviral therapy is a logical treatment strategy and ultrashort, minute, treatments have currently been assessed, as described below Currently, the only compounds recommended as the first line treatment of HSV diseases belong to the class of nucleoside analogues, competitive inhibitor of viral DNA polymerase. Acyclovir and penciclovir are current active principles used in the herpes labialis treatment. Acyclovir has been shown to be the most potent antiviral drug to treat herpes infection.

Several different formulations of acyclovir have been developed for the treatment or prevention of herpes infections: acyclovir 200 mg tablets, 5% acyclovir cream or acyclovir suspension for perfusion. Systemic bioavailability of the drug following administration via oral or topical routes is far from being optimal. The oral absorption of acyclovir is low and highly variable, leading to a poor bioavailability ranging from 15 to 30%. The percutaneous absorption of the 5% acyclovir cream is even poorer with limited transfer of the compound through the mucosa and the skin. The perfusion use is restricted to systemic infections occurring in immunocompromised patients.

In immunocompetent patients, a treatment regimen of acyclovir is 200 mg oral tablets, 5 times daily for 5 days. This treatment showed reduction of time for the loss of the crust (Raborn, J. Am. Dent. Assoc, 1987). However, acyclovir treatment is frequently prolonged due to its incomplete effect. Furthermore, studies have shown that this treatment had no effect on the duration of pain or the time to recovery (Raborn, Oral Surg Oral Med Oral Pathol Oral Radiol Endod, 1997).

Spruance et al. evaluated a regimen of 400 mg of oral acyclovir 5 times daily for 5 days (Spruance, J. Infect. Dis. 1990). Overall in this study, acyclovir reduces the pain and the time of lesion healing. However, a strong inconvenient of these two treatments is their incompliance for patient who have to take these tablets 5 times daily for 5 days.

In frequently recurrent herpes labialis (more than 5 occurrences per year), prophylactic treatment with acyclovir tablets is recommended (Rooney, Annals of Internal Medicine, 2004). Such treatment is, however, very inconvenient for patient since they have to take acyclovir tablets of 400 mg twice daily for 4 months. Currently, the only known prophylactic treatment of frequently recurrent herpes labialis is regular administration of antiviral tablet for a prolonged period of time (4 to 6 months).

The need for a drug with improved pharmacokinetic profile and clinical efficacy led to the development of valacyclovir (L-valine ester of acyclovir), a prodrug of acyclovir with increased bioavailability (absolute bioavailability of acyclovir following oral administration of valacyclovir: 54%). Valacyclovir is administrated via oral route (for instance Valtrex®: containing 500 mg or 1000 mg of valacyclovir hydrochloride or Zeliterx®: containing 500 mg of valaciclovir Chlorhydrate) Likewise, famciclovir, a prodrug of pencyclovir—(diacetyl ester of 6-deoxy pencyclovir, the oral form of penciclovir with an absolute bioavailability of penciclovir following oral administration of famciclovir of 77%) has been developed and registered for the early treatment of labial herpes. Recently, oral 4 g valacyclovir in 2 divided doses of valacyclovir (Valtrex® 2 g twice daily for one day) (Spotswood L. Journal of Antimicrobial Chemotherapy, 2004) and 1.5 g famciclovir are administered within the first hour following prodromal symptoms of herpes labialis. These two treatments were efficient with high systemic doses administered early on for a short duration therapy. These treatments have been shown to induce a reduction of time to lesion healing versus placebo.

To summarize, valacyclovir or famciclovir-based are oral treatments applied one or two times per day with high dosages (1.5 g or 4 g). These treatments show different drawbacks. Indeed, although reducing time to lesion healing, they do not prevent vesicular lesion and do not allow alleviation of rapid pain and other symptoms. Furthermore, side effect, and notably headaches (in about 10% of treated patients) and/or nausea, are frequently reported, irrespective of the dosage and duration of treatment (Spruance, Antimicrob Agents Chemother 2003).

Topical treatments, such as ointments, are often the preferred option. Indeed, they allow an increased concentration of the active principle at the replication site and/or lesion sites. Presently, for patients developing orofacial herpes (1 to 5 episodes yearly), acyclovir or penciclovir creams or ointments are largely used due to their availability as over-the-counter or preparations without prescription in several countries. This also allows avoiding delays to obtain the mandatory prescriptions, which are required for oral acyclovir and valacyclovir. Although acyclovir in the cream or ointment vehicle had some effect in making cold sore lesions heal more quickly, it was not able to prevent cold sore lesions from arising, even when applied at the prodromal stage. The phenomenon of treatment-induced prevention of lesions is also referred to as "aborted lesions" and represents the holy grail of herpes simplex treatment (Spruance, Antimicrob. Agents Chemother. 2002). Such creams or ointments seem to be more active at the vesicular stage, because of easier transfer through the vesicular membrane or moisterizing properties. Several studies investigated the effects of acyclovir cream. However, none of them reported a decrease in the duration or severity of pain according to consensus (Opsteltel, Can Fam Physician 2008). Furthermore, the topical treatments demonstrated limited efficacy and required multiple applications over several days (Spruance, Herpes, 2002). Some studies have suggested that this limited efficacy is the result of inadequate penetration of the drug in the basal epidermis (Parry, J. Invest Dermatol, 1992). Finally, topical treatments are also incompliant for patients. For instance, patients have to apply topical penciclovir 1% cream every 2 hours during waking hours for 4 days or topical acyclovir 5% cream 5 times daily for 5 days.

International patent application WO2009/115510 relates to topical compositions comprising acyclovir, penciclovir and/or omaciclovir as the active principle. Conveniently, treatment with the composition of the invention is commenced as soon as the first sign of a herpes reoccurrence is detected, such as a tingling of the oral lesion or other manifestation of the prodromal stage. Advantageously the treatment results in an aborted lesion. It needs to be applied five times daily and continued for five days.

Again, the recommended 5 daily applications for 5 days raises the issue of patient compliance. Furthermore, topical treatments have poor effects on pain and could generate local irritation.

Therefore, there is a need for another treatment and/or prevention for herpes labialis which also allows compliance for the patient, reduces global symptoms and/or is well tolerated.

Except for the oral (tablet or capsule) or the topical (cream or ointment) route, no other route of administration has been explored to improve bioavailability of acyclovir and/or increase the concentration at replication sites and/or lesion sites.

Therefore, it is an object of the present invention to fulfil said needs with a composition suitable to mucosal delivery of acyclovir and notably a labial and orofacial delivery.

Therefore it is also an object of the present invention to overcome the other deficiencies in the prior art of herpes labialis treatment.

SUMMARY OF THE INVENTION

The present invention relates to a prolonged release mucoadhesive buccal tablet for use in the treatment or prevention of orofacial herpes wherein a single dose is applied.

In another aspect the present invention relates to a prolonged release mucoadhesive buccal tablet comprising at least one acyclic guanosine antiviral agent, 1 to 75% by weight of a diluent, and 1 to 10% by weight of an alkali metal alkylsulfate, 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5% to 80% by weight of at least one polymer that provides a sustained release of acyclic guanosine antiviral agent.

The prolonged release mucoadhesive buccal tablet can be used in a long term efficient treatment of prevention or reduction of the duration of abortive episodes, for reduction of the duration of abortive episodes, for use in reduction of the duration of orofacial herpes episodes, for use in reduction of the occurrence of secondary vesicular lesions, for the treatment of orofacial herpes without significant side effect due to said composition, for use in reduction of the time of healing of primary or secondary vesicular lesions, for use in reduction of global symptoms intensity of orofacial herpes, for use in reduction of salivary viral load and thus local viral spread, intra-individual and/or inter-individual viral transmission, and/or for use at the prodromal stage of herpes labialis.

In another aspect the present invention relates to a prolonged release mucoadhesive buccal tablet comprising at least one acyclic guanosine antiviral agent, 1 to 75% by weight of a diluent, and 1 to 10% by weight of an alkali metal alkylsulfate, 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5% to 80% by weight of at least one polymer that provides a sustained release of the at least one acyclic guanosine antiviral agent.

In yet another aspect the present invention provides a prolonged release mucoadhesive buccal tablet according to claim 14 comprising at least one acyclic guanosine antiviral agent, 1 to 75% by weight of a diluent, and 1 to 10% by weight of an alkali metal alkylsulfate, 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5% to 80% by weight of at least one polymer that provides a sustained release of the active principle for use in the treatment of orofacial herpes.

Yet another aspect of the present invention is a prolonged release mucoadhesive buccal tablet according to claim 16 comprising at least one acyclic guanosine antiviral agent, 1 to 75% by weight of a diluent, and 1 to 10% by weight of an alkali metal alkylsulfate, 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5% to 80% by weight of at least one polymer that provides a sustained release of the at least one acyclic guanosine antiviral agent.

DESCRIPTION OF THE PREFERRED EMBODIMENTS OF THE INVENTION

Figure 1:
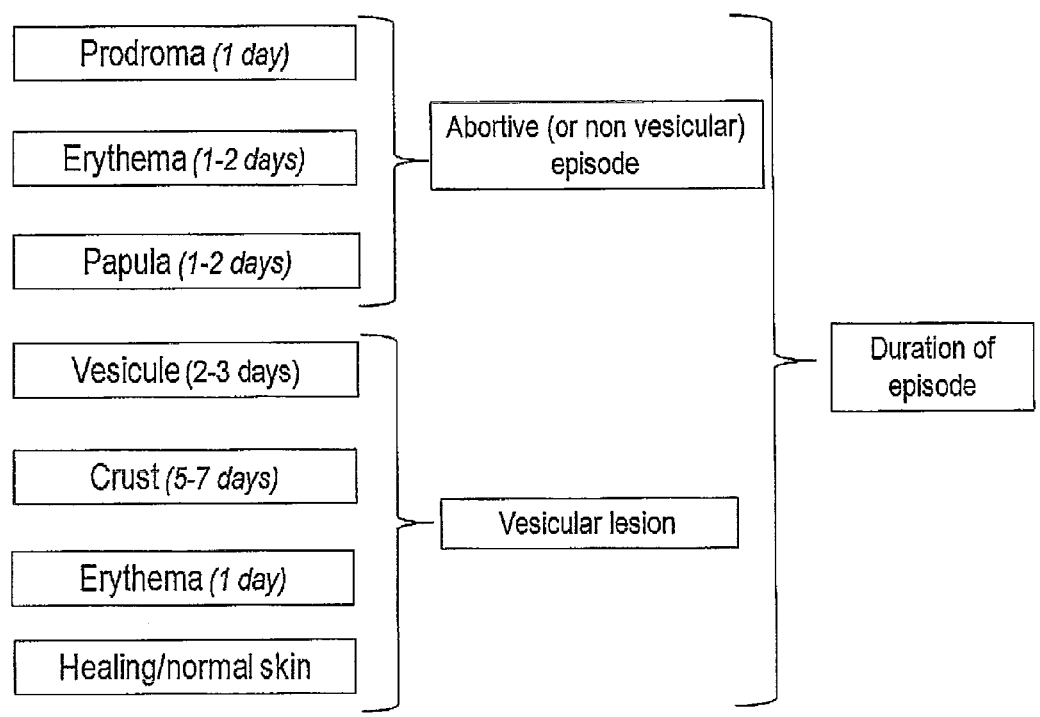
FIG. 1 is a schematic representation of the evolution of herpes labialis pathology
Figure 2:
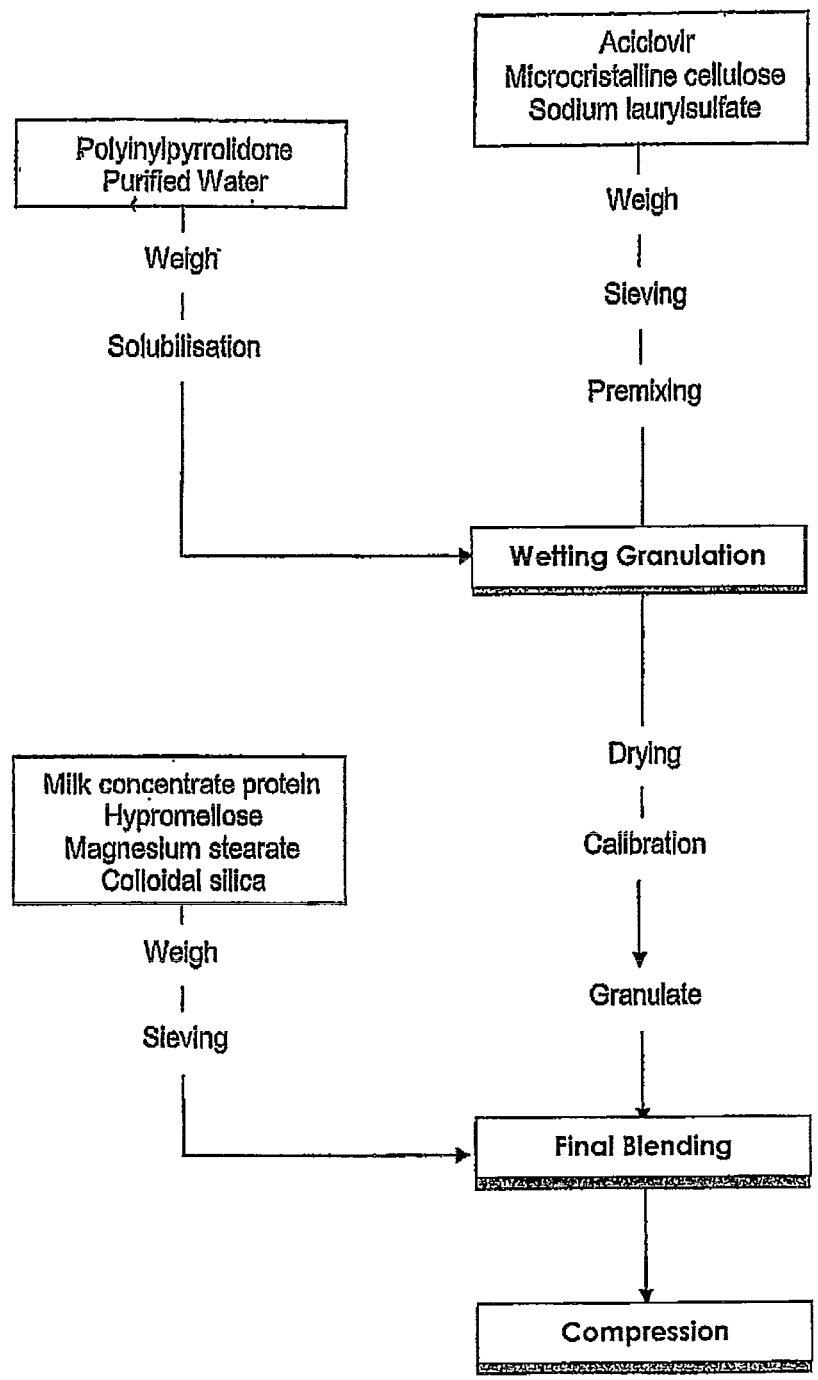
FIG. 2 is a schematic representation of the process to produce the prolonged release mucoadhesive buccal tablet of the present invention.
Figure 3:
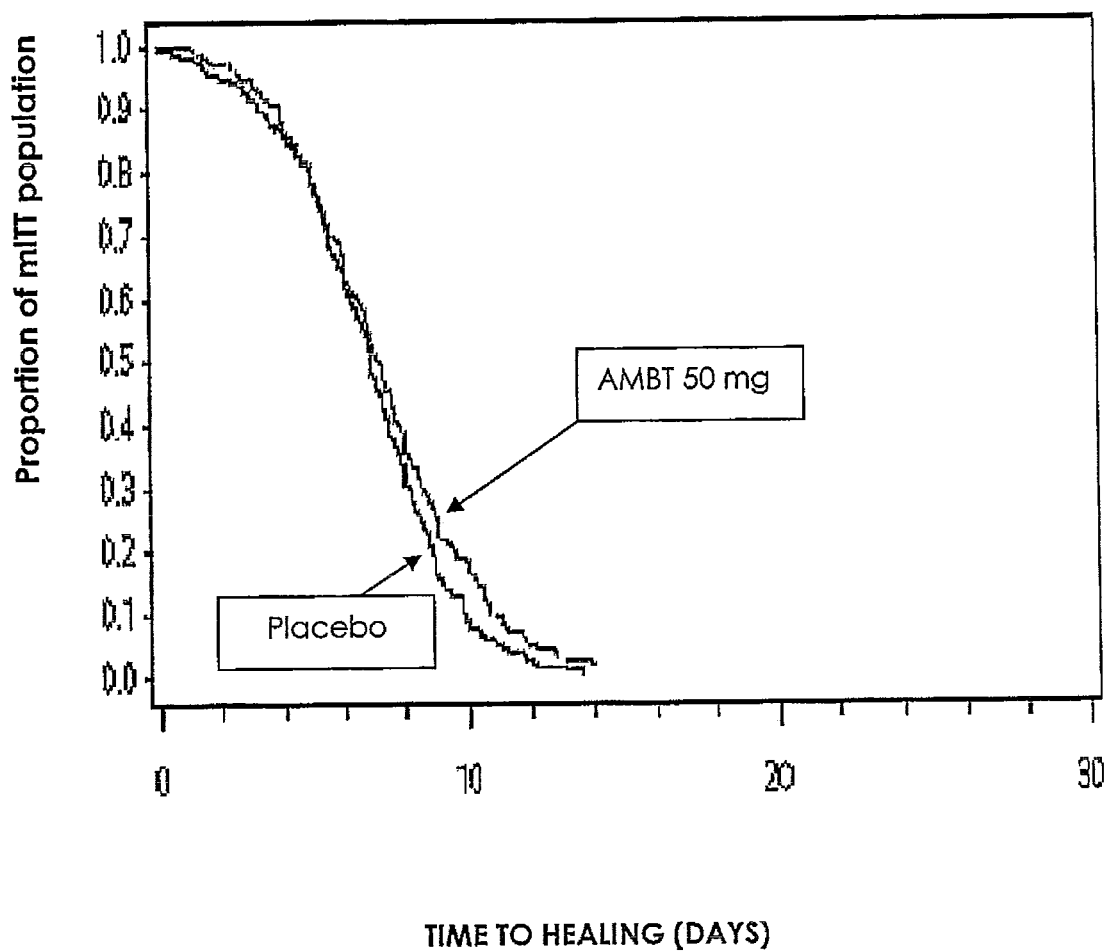
FIG. 3 represents the time to healing in mITT population
Figure 4:
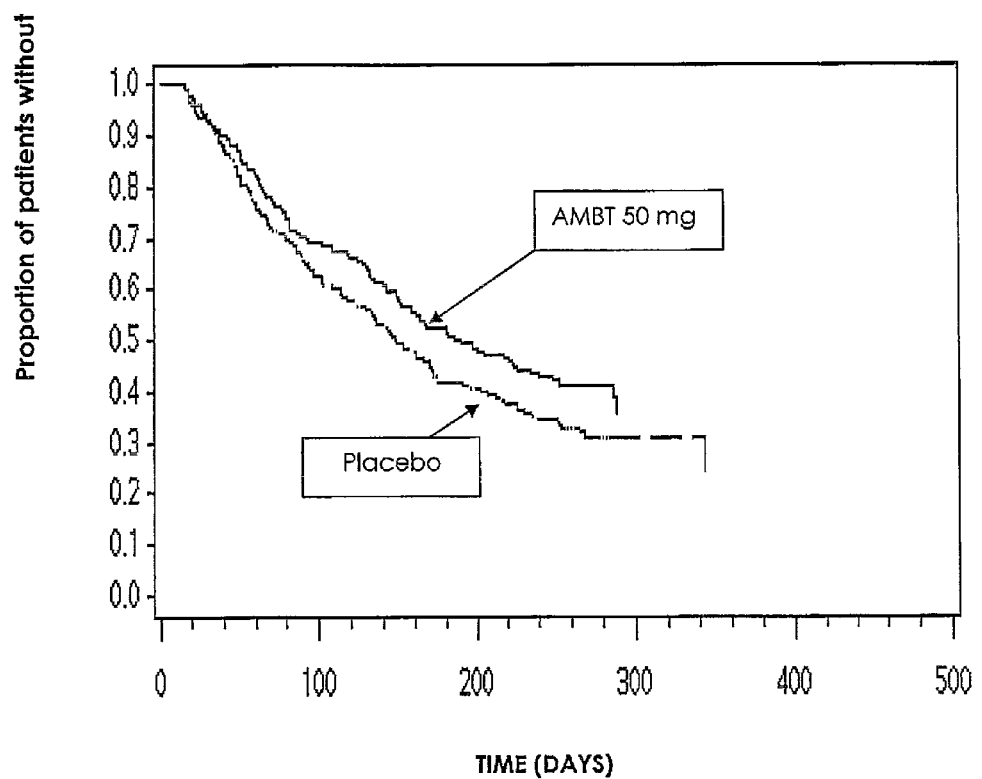
FIG. 4 represents the proportion of patients without recurrence of herpes labialis.

The term "mucocutaneous" means a zone of skin comprising both mucosa and cutaneous skin. These mostly occur near the orifices, at the lips for instance.

The term "buccal" means of, relating to, involving or lying in the mouth.

The term "treatment" means alleviating, inhibiting the progress of, or curing orofacial herpes, or one or more symptoms of orofacial herpes.

The term "symptoms" means itching, tingling, pain, burning, discomfort and tenderness.

The term "prevention" means reducing the frequency of recurrence of orofacial herpes.

The term "long term prevention" means reducing the frequency of recurrence of Orofacial herpes at least 9 months after the last occurrence.

Similarly, throughout the text, the expression "prolonged release"; "slow release" or "sustained release" are used interchangeably and mean that the active principle is released immediately after 30 minutes and then over a prolonged period of time of at least 15 hours or at least 18 hours or at least 20 hours or at least 24 hours and up to 36 hours.

The term "occurrence" means the beginning of an episode of orofacial herpes.

The term "recurrence" means the occurrence of new episode of orofacial herpes, after the healing of all lesions of the initial episode of orofacial herpes The expression "frequently recurrent orofacial herpes" means more than 5 occurrences per year.

The expression "severe orofacial herpes" means persistent and/or spread lesions in particular in the immunocompromized patient.

"Orofacial herpes" means an herpes with facial or cutaneous or mucosal lesions or stomatitis.

The expression "time to recurrence" means the time from the healing of all lesions of the initial episode of orofacial herpes to the occurrence of new lesions.

The expression "primary vesicular lesion" is the first developed lesion which should be located on the lip and should not extend more than 1 cm outside the lip. Pure intra-oral lesions are not considered as primary lesions.

The expression "aborted lesions" means herpetic lesions preceded by prodromal symptoms that do not progress beyond the papule stage.

The expression "secondary lesions" means the lesions developed in addition to and/or in 1 or more days after the primary lesion and that are located at least 1 cm from the primary lesion.

The expression "duration of episode" means the time from the beginning of prodromal symptoms to the healing of primary and secondary lesions.

The expression "duration of abortive episode" means the time from the beginning of prodromal symptoms to the healing of the papula lesions.

The expression "time to cessation of symptoms" means the time from the treatment initiation to the cessation of all symptoms: pain, burning, itching, tingling, tenderness and discomfort.

The expression "time to healing of aborted primary lesions (TTH)" means the time from the treatment initiation to the healing of primary lesion or cessation of symptoms, whichever comes last.

The expression "time to healing of intra-oral/mucosal secondary lesions" means the time from the treatment initiation to healing of intra-oral/mucosal non primary lesions.

The term "healing" means the loss of crust. Erythema may be present following the loss of crust.

The expression "time to healing" means the time from the treatment initiation (date and hour recorded) to the healing.

The expression "ITT Population" means all randomized patients who took at least one dose of the study medication.

The expression "mITT population" means all randomized patients who took at least one dose of the study medication and who reached the vesicular stage.

The expression "PP population" means all patients of the mITT population who did not have a major protocol deviation. The prolonged release mucoadhesive buccal tablets of the invention are described in the patent application US20090169511, incorporated herein by reference.

The invention relates to the use of the prolonged release mucoadhesive buccal tablets for mucosal, notably labial, slow release of acyclic guanosine antiviral agents for the treatment of orofacial herpes. Said prolonged release mucoadhesive buccal tablets have many advantages as described below.

The main general advantage of the prolonged release mucoadhesive buccal tablets of the invention is to allow a rapid release (30 minutes after application) of acyclic guanosine antiviral agents in saliva and for a long duration (more than 24 hours). As demonstrated below, this advantageous kinetic release leads to an early (in the first days) and prolonged (within at least 9 months) efficient treatment and/or prevention of orofacial herpes. Furthermore the prolonged release mucoadhesive buccal tablets of the invention are used at a single dose and surprisingly afford several kinds of relief for patients undergoing orofacial herpes. This single dose allows a much better compliance for patients, compared to the treatments of the state of the art and notably to the current topical treatments, needing application five times daily and continued for five (or more) days.

Another embodiment of the invention is to provide prolonged release mucoadhesive buccal tablets for the treatment of orofacial herpes with a low dose of acyclovir. This low dose is comprised between 10 to 200 mg per tablet and 50 mg is preferred. Hence the mucoadhesive buccal tablets of the invention allow an efficient treatment and/or prevention with a low active principle dosage. It is surprising in comparison to the current treatments where high doses of active principle are preferred. An unexpected efficacy with respect to aborted lesions has been shown. Indeed, when applied on patients undergoing the prodromal symptom, the mucoadhesive buccal tablets of the invention substantially reduce the number of patients who progress beyond the papule stage. In other words the number of patients that enter the vesicular lesion stage is substantially reduced. This result is all the more noteworthy since it is obtained with a single dose. Hence, an object of the invention is to provide prolonged release mucoadhesive buccal tablets for the treatment of orofacial herpes at the prodromal stage. As orofacial herpes is most contagious at the vesicular stage, it is another advantage of the prolonged release mucoadhesive buccal tablets of the invention to reduce the risk of transmission of the virus by limiting the occurrence of vesicular lesions.

It has also been demonstrated that the mucoadhesive buccal tablets of the invention reduce the duration of abortive episodes. Thus another aspect of the invention relates to the use of prolonged release mucoadhesive buccal tablets on patients undergoing the prodromal symptom to decrease the duration of abortive episodes.

A further aspect of the invention is to provide prolonged release mucoadhesive buccal tablets to reduce the duration of orofacial herpes episodes. Indeed, a remarkable decrease of the global duration of episodes has been demonstrated. Since this effect has been observed on the global duration of episodes, it is expected that the prolonged release mucoadhesive buccal tablets of the invention can be therapeutically efficient even if applied after the prodromal stage.

Another aspect of the invention relates to prolonged release mucoadhesive buccal tablets for reducing the duration or severity of symptoms (itching, tingling, pain, burning, discomfort, and/or tenderness) induced by herpes labialis. Surprisingly, the prolonged release mucoadhesive buccal tablets show an early efficacy. Indeed, significant reduction of global symptom intensity begins at day 3 (thus during the abortive episode, as defined in FIG. 1) and is the most significant at day 5.

More precisely, studies conducted herein have demonstrated that the time of cessation of symptoms is about 0.4 days shorter with the prolonged release mucoadhesive buccal tablets of the invention than with placebo.

A further embodiment of the invention relates to prolonged release mucoadhesive buccal tablets for the treatment of orofacial herpes by reducing the occurrence of secondary vesicular lesions. Indeed, it has been showed that the prolonged release mucoadhesive buccal tablets reduces the occurrence of secondary lesions by nearly 50% as compared to placebo.

Another embodiment of the invention is to provide prolonged release mucoadhesive buccal tablets for the treatment of orofacial herpes without adverse side effects due to acyclovir. Indeed prolonged release mucoadhesive buccal tablets of the invention are extremely well tolerated and present very limited systemic effects (notably diarrhea, headache) and, contrary to the current topical treatments, do not induce local irritation.

A further aspect of the invention is to provide prolonged release mucoadhesive buccal tablets for the treatment of orofacial herpes by significantly reducing the time of healing of primary vesicular lesion.

More precisely, studies conducted herein have demonstrated that the time of healing is about 0.4 days less than placebo.

Another aspect of the invention relates to prolonged release mucoadhesive buccal tablets for the treatment of orofacial herpes by reducing the recurrence of abortive episodes or episodes. Indeed, it has been shown herein for the first time prevention of the recurrence of vesicular lesions. Prolonged release mucoadhesive buccal tablets of the invention are thus particularly suitable for the treatment of recurrent orofacial herpes or severe orofacial herpes.

Another object of invention is to provide prolonged release mucoadhesive buccal tablets for an early or short term efficient treatment or prevention of abortive episodes or episodes.

Another object of invention is to provide prolonged release mucoadhesive buccal tablets for the treatment of frequently recurrent and/or severe orofacial herpes especially for immunocompromized patients.

The prolonged release mucoadhesive buccal tablets of the invention are also suitable for the treatment of not only cutaneous lesions but also mucosally, spread, lesions. It is another object of the invention to provide the use of prolonged release mucoadhesive buccal tablets for mucosal delivery of acyclovir allowing maintaining efficacious concentrations of acyclic guanosine antiviral agents in the viral reservoir, decreasing local viral spread and thus intra-individual and inter-individual viral transmission.

Indeed, besides early and prolonged efficient concentrations of acyclic guanosine antiviral agents in the saliva, the prolonged release mucoadhesive buccal tablets of the invention allow early and prolonged efficient concentrations of acyclic guanosine antiviral agents in the mucous, epidermis and/or trigeminal ganglions.

Another embodiment of the invention is to provide prolonged release mucoadhesive buccal tablets for the treatment of orofacial herpes with a low dose of acyclovir. Said low dose is comprised between 10 to 200 mg per tablet, while 50 mg is preferred.

It is another aspect of the invention to provide the use of prolonged release mucoadhesive buccal tablets for mucosal delivery of acyclovir allowing an early and sustained release of acyclovir at the infection site to exert a "continuous antiviral pressure" against HSV-1.

Another aspect of the invention is to provide the use of prolonged release mucoadhesive buccal tablets for mucosal delivery of acyclovir attached to the buccal cavity, retained for a longer period of time and removed at any time, thus allowing flexibility of use.

It is another aspect of the invention to provide the use of prolonged release mucoadhesive buccal tablets for mucosal delivery of acyclovir which can be applied at different sites in the oral cavity, preferably at the gum.

The prolonged release mucoadhesive buccal tablets of the invention are described in patent application US20090169511, incorporated herein by reference.

These prolonged release mucoadhesive buccal tablets at least one acyclic guanosine antiviral agent, 1 to 75% by weight of a diluent, and 1 to 10% by weight of an alkali metal alkylsulfate, 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5% to 80% by weight of at least one polymer that provides a sustained release of the acyclic guanosine antiviral agents.

Examples of diluents include microcrystalline cellulose, silicified microcrystalline cellulose, hydroxymethylcellulose, dicalcium phosphate, calcium carbonate, calcium sulfate, magnesium carbonate, tricalcium phosphate, lactose, starck and the like. The diluent is present in an amount between 1 and 75% by weight in the bioadhesive slow release carrier.

An alkali metal alkylsulfate is also a component of the prolonged release mucoadhesive buccal tablets of the present invention. This alkali metal sulfate improves the granulation of the active principle acting as a solubilization agent. The alkali metal alkylsulfate that can be used in the formulation includes magnesium lauryl sulfate, potassium lauryl sulfate, sodium laurylsulfate and diethylsulphosuccinate. Generally it is present in the prolonged release mucoadhesive buccal tablets at a concentration of between 1 to 10% by weight, 2% to 10% by weight or 2 to 6% by weight.

The binders used in the present invention can be selected from carboxy vinyl polymer, methycellulose, hydroxyethylcellulose, hydroxypropyl cellulose, gumarabic, starch, hydroxypropylmethylcellulose, polyvinylpyrrolidone, polyethylene glycol and the like. The binders are present in the amount of 0.1 to 5% by weight in the bioadhesive slow release carrier.

The bioadhesive polymers are selected from the group of:
natural polymers:
Polysaccharides: chitosan, alginate, carboxymethyl cellulose, hydroxypropyl methyl cellulose (also called hypromellose), hydroxyethyl cellulose, hydroxypropyl cellulose, cyclodextrin, sodium hyaluronate, xanthum gum, Natural proteins: from animal origin or vegetable origin, natural milk proteins, natural pea proteins, natural soy proteins, natural potato proteins, natural wheat proteins, gliadin proteins, synthetic polymers: carbomer, polyvinylalcohol, acrylic polymers.

The bioadhesive polymers are present in the prolonged release mucoadhesive buccal tablets prolonged release mucoadhesive buccal tablets at a concentration of 5 to 80% by weight. They can also be present in an amount of 10% to 40% by weight. Regarding the natural milk proteins, these are described in EP 0 542 824. They can be obtained from pasteurized raw milk and include total milk proteins, casein protein concentrates and whey protein concentrates. The total milk proteins are recovered from skimmed milk after ultra-filtration. The casein protein products are obtained by insolubilizing the casein in milk at its isoelectric point, and further washing and drying the casein. The whey protein concentrates are obtained after coagulating cheese with enzymes and separating the yellow-green liquid residue out, which residue is whey. The whey is then further concentrated by ultrafiltration, ion exchange chromatography or thermal precipitation. Regarding the vegetable proteins, they can be obtained from pea, soy, potato, wheat or gliadin. The method for producing pea protein is described in WO 2007/017571.

The sustained release polymers that can be used in the prolonged release mucoadhesive buccal tablets include hydrophilic polymers including polysaccharides such as cellulose ethers, xanthum gum, scleroglucan, locust bean gum, gum Arabic, gum tragacanth, carob, alginic acid, alginates, carrageenates, agar-agar and guar gum either alone or in mixtures thereof. Other polymers that can be used in the present invention include cellulose based polymers such as hypromellose (also named hydroxypropyl methyl cellulose), cellulose acetate, cellulose esters, cellobiose, cellulose resins alone or in mixtures thereof. The sustained release polymers are present in a concentration of 5% to 80% by weight. They can also be present in an amount of 10% to 40% by weight.

In another embodiment the present invention relates to a mucosal bioadhesive slow release carrier comprising 10 to 200 mg of acyclovir, 1 to 75% by weight of a diluent of microcrystalline cellulose and 2 to 10% by weight of sodium lauryl sulphate and further comprising 0.1 to 5% by weight of a polyvinylpyrrolidine and 10 to 40% by weight of at least one bioadhesive polymer selected from the group of natural milk proteins and mixtures thereof and 10% to 40% by weight of hypromellose.

Magnesium stearate between 0.1 to 5% and colloidal silica between 0.1 to 1% can be added to the mucosal bioadhesive slow release carrier to facilitate the process of preparation. The at least one acyclic guanosine antiviral agent is preferably acyclovir.

The mucosal bioadhesive slow release carrier used in the present invention permits the immediate local liberation of the active principle, as well as the prolonged liberation of the active principle and then provides an early and prolonged efficacy.

The preferred embodiment of the invention is a prolonged release mucoadhesive buccal tablets comprising 50 mg of acyclovir, 15% by weight microcrystalline cellulose, 4.5% by weight of sodium lauryl and further comprising 0.4% by weight of polyvinylpyrrolidine, 20% by weight of milk concentrate protein, 15% by weight of hypromellose, 0.5% by weight of magnesium stearate and 0.4% by weight of colloidal silica.

A method for preparing said prolonged release mucoadhesive buccal tablets comprises:

a) granulating a mixture of at least one acyclic guanosine antiviral agent with an alkali metal alkylsulfate, a diluent and a binding agent;
b) blending said granulated mixture with at least one bioadhesive polymer, at least one sustained release polymer and at least one compression agent; and
c) compressing the blended mixture obtained in b).

In yet another aspect the present invention provides a method for delivering at least one acyclic guanosine antiviral agent to a mammal, said method comprising mucosally administering to a mammal in need of said at least one acyclic guanosine antiviral agent, a bioadhesive slow release carrier comprising at least one acyclic guanosine antiviral agent, 1 to 75% by weight of a diluent and 1 to 10% by weight of an alkali metal alkylsulfate 0.1 to 5% by weight of a binding agent, 5 to 80% by weight of at least one bioadhesive polymer selected from the group of natural polymers wherein said natural polymers are polysaccharides or, natural proteins from animal origin or vegetable origin or, synthetic polymers, and mixtures thereof and further comprising 5 to 80% by weight of at least one polymer that provides a sustained release of the at least one acyclic guanosine antiviral agent.

A number of embodiments of the invention have been described. Nevertheless, it will be understood that various modifications may be made without departing from the spirit and scope of the invention.

EXAMPLES

Example 1

Preparation of a Prolonged Release Mucoadhesive Buccal Tablet Containing 50 mg of Acyclovir 50 mg of acyclovir, 15% by weight microcrystalline cellulose and 4.5% by weight of sodium lauryl sulfate were weighed and sieved with a 0.7 to 2 mm sieve before premixing in a blender to provide the "initial mix."

At the same time, 0.4% by weight polyvinylpyrrolidone was dissolved in purified water: The resulting solution was added to the initial mix and further stirred. The wetted mixture was then granulated using a pharmaceutical mixer or granulator such as a planetary mixer or high sear mixer and dried and then calibrated to 0.5 to 2 mm. The resulting pellets formed the "primary granules."

20% milk concentrate protein, 15% hypromellose, 0.5% magnesium stearate and 0.4% of colloidal silica were weighed and sieved using a 0.5 to 2 mm sieve. These ingredients were then added to the primary granulation to form the "final blending" mixture. The final blending mixture was then compressed using a tablet press such as a rotative press to produce the compressed carriers according to the invention.

The size of the tablets was about 8 to 10 mm in diameter. The dimension was chosen to be comfortable in the canine fossa.

Example 2

Investigational Plan

A randomised, double-blind, single dose multicenter study comparing a single dose treatment of "acyclovir Lauriad® 50 mg", the prolonged release mucoadhesive buccal tablets of Example 1 (hereinafter referred to as AMBT 50 mg), versus matching placebo (randomisation in a 1:1 ratio) in immunocompetent patients suffering from recurrent orofacial herpes was carried out.

The study was carried out at multiple centers that treat patients with orofacial herpes. Approximately 1730 patients who meet the inclusion/exclusion criteria, were randomised according to a 1:1 ratio to receive either a single dose of AMBT 50 mg, or matching placebo. Only those patients having an episode of orofacial herpes in the 6 months following randomisation had applied the tablets. It was calculated that 780 patients (390/group) had to be included to adequately compare the efficacy of AMBT 50 mg to placebo; 1170 patients were therefore randomised and not treated.

The study duration for each patient included a screening period of 10 days maximum before randomisation. The patient then waited for a new orofacial herpes episode to occur (up to a maximum of 6 months). If the patient did not experience an episode of orofacial herpes within 6 months after randomisation he/she was excluded from the study. As soon as the patient experienced prodromal symptoms, he/she self-initiated his/her treatment. The patient was under evaluation up to Day 14, or up to the healing of primary lesions, whichever came first. For those patients in which the treatment was initiated, the maximum patient participation duration was 204 days (including the 6 months period). In some selected centers, patients were required to record the number of new episodes and the time to their recurrence for a period of 9 months.

For patients who were not treated because of the absence of recurrence of orofacial herpes in the 6 months following randomisation, the patient participation was 190 days.

Inclusion Criteria

Patients were randomised provided that they satisfied the following criteria:
  Male or female;
  Age>18 years;
  History of recurrent herpes labialis lesions where:
    Recurrence was defined as at least 4 episodes in the preceding 12 months;
    Herpes labialis lesions were characterised by their localisation on the cutaneous and/or mucosal surfaces of the lips;
  At least 50% of previous episodes produced classical lesions progressing to the vesicular stage (i.e., episodes that progressed through macula, papule, vesicle, crust and healing);
  Prodromal symptoms (itching, tingling, pain etc.) preceded herpes labialis lesions in at least 50% of the recurrent episodes;
  Good general health (ECOG<2), immunocompetent;
  Signed and dated written informed consent;
  Women of childbearing potential were included provided that they use an highly effective contraception method: hormonal contraception, implantable contraceptive, injectable contraceptive double-barrier method (diaphragm with spermicide, codom with spermicide) or intrauterine device, at least 1 month prior to study start and throughout the entire duration of the study;
  Subjects had to agree to abstain from any mechanical disruption of the prodromal area or lesion (i.e. scrubbing, lancing, shaving the area, rubbing with alcohol, . . . ).

Endpoints

To demonstrate the efficacy of a single dose of AMBT 50 mg versus a single dose of matching placebo of herpes labialis the endpoints were:
  The evolution of prodromal symptoms to aborted lesions;
  The healing of primary lesions;
  The healing of non primary lesions;
  The duration of episode;
  The duration of symptoms;
  The intensity of global symptoms;
  The healing of aborted lesions;
  The healing of intra-oral and mucosal lesions;
  The incidence of and time to recurrence during 9 months following treatment (ancillary study in selected centers);
  The comparison of the local tolerability and general safety of AMBT 50 mg to those of placebo;
  The evaluation of the concentration of acyclovir in saliva (ancillary study in selected centres) and the assessment of its relationship with viral load in saliva and efficacy criteria;
  To evaluate the adhesion time of AMBT 50 mg, the incidence of detachment and/or swallow and the number of tablets replaced.

Adverse Events

An adverse event was considered as drug related if a causal relationship could not be excluded. In case of missing causal relationship the adverse event was considered drug related.

Treatment emergent adverse events (TEAE) was evaluated. A TEAE is defined as:
  An adverse event that occurs after starting the study treatment and that was not present before administration of the study treatment;
  An event that was present before study treatment but worsened in intensity or frequency after administration of the study treatment.

The treatment emergent period went from treatment administration to the end of the study.

A patient listing of all reported adverse events was prepared.

Haematology and Biochemistry Parameters

A descriptive analysis by treatment group was performed. Abnormal values considered as clinically significant were identified.

Local Tolerability

A descriptive analysis by treatment group was performed.

Compliance

A detailed description was made regarding compliance and the duration of the two treatments. Comparison of compliance and treatment duration between the two groups was made.

Results

Patient Population

| Patients | AMBT 50 mg | Placebo | Total |
| --- | --- | --- | --- |
| Screened | | | 1944 |
| Treated | 378 (100%) | 397 (100%) | 775 (44.9%) |
| ITT | 376 (99.5%) | 395 (99.5%) | 771 (99.5%) |
| Completers | 361 (96.0%) | 384 (97.2%) | 745 (96.6%) |
| Vesicular lesions | 245 (64.8%) | 282 (71.3%) | 527 (68.3%) |
| mITT | 189 (50.0%) | 223 (56.4%) | 412 (53.1%) |

The skilled person is able to carry out known statistical analysis method to obtain the following results:

The time to healing of primary vesicular was significantly reduced compared to the placebo

| | AMBT 50 mg | Placebo |
| --- | --- | --- |
| Patients | 189 | 223 |
| Time to healing | 6.77 ± 0.19 | 7.23 ± 0.19 |

AMBT 50 mg prevented the occurrence of significantly vesicular lesions and significantly reduced the duration of non vesicular episodes

|  | AMBT 50 mg | Placebo |
| --- | --- | --- |
| Patients | 350 | 364 |
| N Patient (%) | 73 (20.9%) | 55 (15.1%) |
| Duration (days) | 3.76 ± 0.15 | 4.25 ± 0.16 |

AMBT 50 mg significantly reduced the duration of episodes (aborted episodes and vesicular episodes)

|  | AMBT 50 mg | Placebo |
| --- | --- | --- |
| Patients | 355 | 367 |
| Duration (days) | 5.00 ± 0.17 | 5.62 ± 0.18 |

AMBT 50 mg significantly reduced the duration of orofacial herpes symptoms.

|  | AMBT 50 mg | Placebo |
| --- | --- | --- |
| Patients | 337 | 350 |
| Duration (days) | 3.61 ± 0.15 | 4.06 ± 0.16 |

Reduction of global symptom intensity begun at day 3 and was the most significant at day 5. AMBT 50 mg rapidly decreased pain associated with herpes.

|  | AMBT 50 mg | Placebo |
| --- | --- | --- |
| Patients | 378 | 397 |
| Day 1 (mm) | 30.5 | 31.1 |
| Day 3 (mm) | 21.2 | 22.9 |
| Day 5 (mm) | 12.7 | 17.3 |
| Day 7 (mm) | 8.2 | 10.7 |
| Day 14 (mm) | 1.0 | 0.9 |

AMBT 50 mg significantly reduced the occurrence of secondary lesions

|  | AMBT 50 mg | Placebo |
| --- | --- | --- |
| Patients | 13 | 23 |

AMBT 50 mg was extremely well tolerated, without difference compared to the placebo with respect to diarrhea, headache and/or site irritation and had no effect on haematology and biochemistry parameters.

|  | AMBT 50 mg | Placebo |
| --- | --- | --- |
| Patients | 378 | 397 |

AMBT 50 mg allowed a remarkable difference in term of recurrence of aborted episodes or episodes. Within a follow-up of 9 months, a single dose of AMBT 50 mg showed that said new episode appeared at least 1 month later compared to the placebo.

|  | AMBT 50 mg | Placebo |
| --- | --- | --- |
| Median (days) | 186 | 149 |

Furthermore, AMBT 50 mg significantly reduced the risk of transmission of the virus by limiting the occurrence of vesicular lesions.

To summarize, the complete evaluation of the study is demonstrative regarding the primary endpoint Time to healing of primary vesicular lesion with a p=0.043, secondary endpoints (less patients presenting vesicular lesions in the course of the infection and shorter global duration of the episode, decreased intensity of symptoms) were also significant. The tolerance was remarkable. The long term follow up showed a clear trend to prevent recurrence of episodes at 9 months.

The invention claimed is:

1. A method for treating orofacial herpes comprising administering to a patient suffering from orofacial herpes only a single dose of a prolonged release mucoadhesive buccal tablet comprising:
    50 to 200 mg of acyclovir,
    1 to 75% by weight of a diluent,
    1 to 10% by weight of an alkali metal alkylsulfate,
    0.1 to 5% by weight of a binding agent,
    5 to 80% by weight of natural milk proteins, and
    5% to 80% by weight of at least one hydrophilic polymer that provides a sustained release of acyclovir.

2. The method of claim 1, wherein the acyclovir is present in an amount of 50 mg.

3. The method of claim 1, wherein the mucoadhesive buccal tablet comprises:
    (a) 2 to 6% by weight of an alkali metal alkylsulfate,
    (b) 0.1 to 5% by weight of a binding agent,
    (c) 10 to 40% by weight of natural milk proteins and
    (d) 10% to 40% by weight of at least one hydrophilic polymer that provides a sustained release of acyclovir.

4. The method of claim 3, wherein the alkali metal alkylsulfate is sodium lauryl sulfate.

5. The method of claim 3, wherein at least one hydrophilic polymer that provides a sustained release of acyclovir is hydroxypropylmethyl cellulose.

6. The method of claim 3, wherein said natural milk proteins comprise milk protein concentrate.

7. The method of claim 3, wherein the acyclovir is present in an amount of 50 mg.

8. The method of claim 1, wherein the mucoadhesive buccal tablet comprises:
    (a) 50 mg acyclovir,
    (b) 15% by weight microcrystalline cellulose,
    (c) 4.5% by weight sodium lauryl sulfate,
    (d) 0.4% by weight polyvinylpyrrolidone,
    (e) 20% by weight milk protein concentrate, and
    (f) 15% by weight hydroxypropylmethyl cellulose.

9. The method of claim 1, wherein said patient is suffering from nonvesicular symptoms of orofacial herpes.

10. The method of claim 8, wherein said patient is suffering from nonvesicular symptoms of orofacial herpes.

11. The method of claim 1, wherein said patient is immunocompetent.

12. The method of claim 8, wherein said patient is immunocompetent.

13. The method of claim 1, wherein said patient is suffering from recurrent orofacial herpes.

14. The method of claim 8, wherein said patient is suffering from recurrent orofacial herpes.

15. The method of claim 1, wherein said mucoadhesive buccal tablet is effective to reduce the duration of orofacial herpes episodes.

16. The method of claim 1, wherein said mucoadhesive buccal tablet is effective to delay the recurrence of orofacial herpes episodes.

17. The method of claim 1, wherein said mucoadhesive buccal tablet is effective to increase the occurrence of aborted episodes of orofacial herpes.

18. The method of claim 1, wherein said natural milk proteins comprise milk protein concentrate.

19. The method of claim 1, wherein said natural milk proteins comprise total milk proteins.

20. The method of claim 3, wherein at least one hydrophilic polymer that provides a sustained release of acyclovir is a polysaccharide.

21. The method of claim 20, wherein at least one hydrophilic polymer that provides a sustained release of acyclovir is a cellulose-based polymer.

22. The method of claim 21, wherein at least one hydrophilic polymer that provides a sustained release of acyclovir is a cellulose ether.

* * * * *

UNITED STATES PATENT AND TRADEMARK OFFICE
CERTIFICATE OF CORRECTION

| | | |
|---|---|---|
| PATENT NO. | : 8,592,434 B2 | Page 1 of 1 |
| APPLICATION NO. | : 12/634225 | |
| DATED | : November 26, 2013 | |
| INVENTOR(S) | : Attali et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 189 days.

Signed and Sealed this
Eighteenth Day of November, 2014

Michelle K. Lee
*Deputy Director of the United States Patent and Trademark Office*